United States Patent [19]
Suorsa et al.

[11] Patent Number: 6,036,647
[45] Date of Patent: Mar. 14, 2000

[54] PZT OFF-APERTURE BONDING TECHNIQUE

[75] Inventors: Veijo Suorsa, Sunnyvale; Donald S. Mamayek, Mountain View, both of Calif.

[73] Assignee: Scimed Life Systems, Inc., Natick, Mass.

[21] Appl. No.: 09/127,994

[22] Filed: Jul. 31, 1998

[51] Int. Cl.[7] .................. A61B 8/14; H04R 17/00
[52] U.S. Cl. .................. 600/459; 600/466; 600/467; 29/25.35
[58] Field of Search .................. 600/459, 447, 600/463, 466, 472, 467; 367/140, 152, 155, 162, 176; 310/327, 358; 29/25.35; 73/642

[56] References Cited

U.S. PATENT DOCUMENTS

| | | | |
|---|---|---|---|
| 4,482,834 | 11/1984 | Dias et al. | 310/327 |
| 5,175,709 | 12/1992 | Slayton et al. | 367/90 |
| 5,381,385 | 1/1995 | Greenstein | 367/140 |
| 5,511,296 | 4/1996 | Dias et al. | 29/25.35 |
| 5,617,865 | 4/1997 | Palczewska et al. | 600/459 |
| 5,655,276 | 8/1997 | Pattanayak et al. | 29/25.35 |
| 5,701,901 | 12/1997 | Lum et al. | 600/462 |
| 5,906,580 | 5/1999 | Kline-Schoder et al. | 600/459 |
| 5,920,972 | 7/1999 | Palczewska et al. | 29/25.35 |

*Primary Examiner*—Francis J. Jaworski
*Assistant Examiner*—Ali M. Imam
*Attorney, Agent, or Firm*—Townsend and Townsend and Crew LLP

[57] ABSTRACT

A transducer assembly having an improved external connection configuration, a method for manufacturing such a transducer assembly, and a catheter system incorporating the transducer assembly. The improved connection configuration is achieved by creating a conductive path from an upper electrode of the transducer to an electrically conductive notch surface formed on an edge of the transducer assembly so that an external electrical lead can be attached to the active portion of the transducer element via the path.

23 Claims, 5 Drawing Sheets

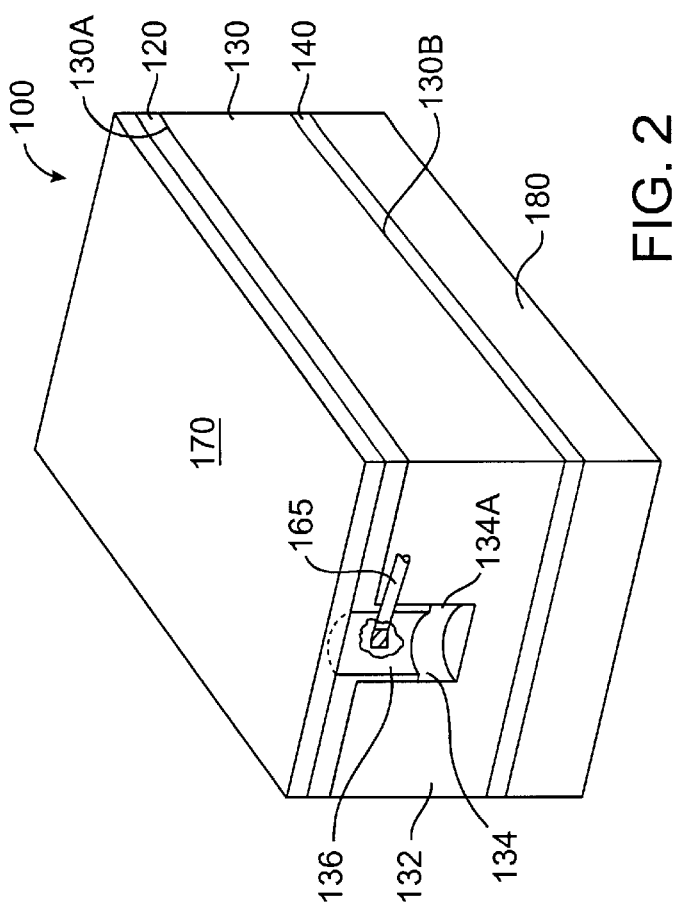
FIG. 2
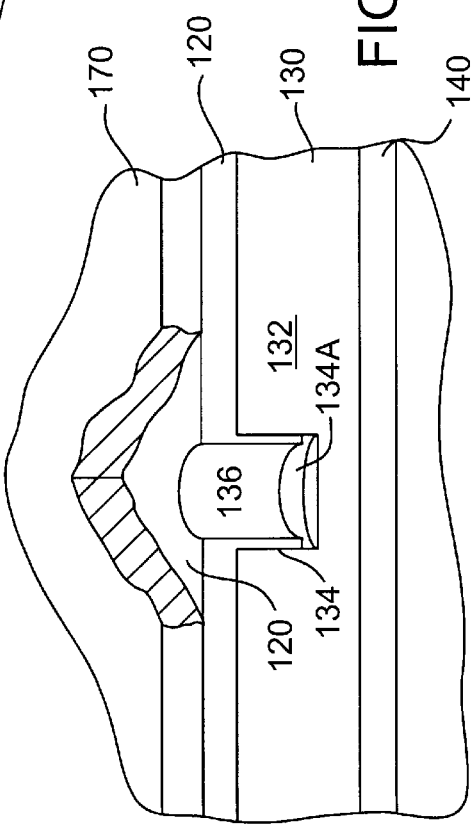
FIG. 2A
FIG. 1C
(PRIOR ART)

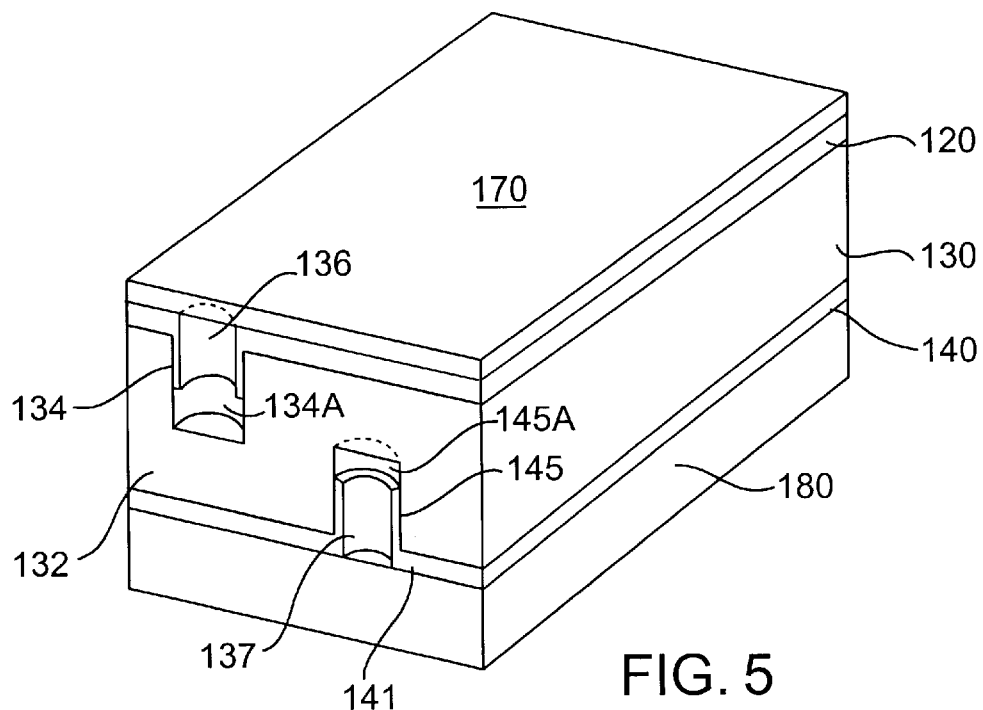
FIG. 5
FIG. 6
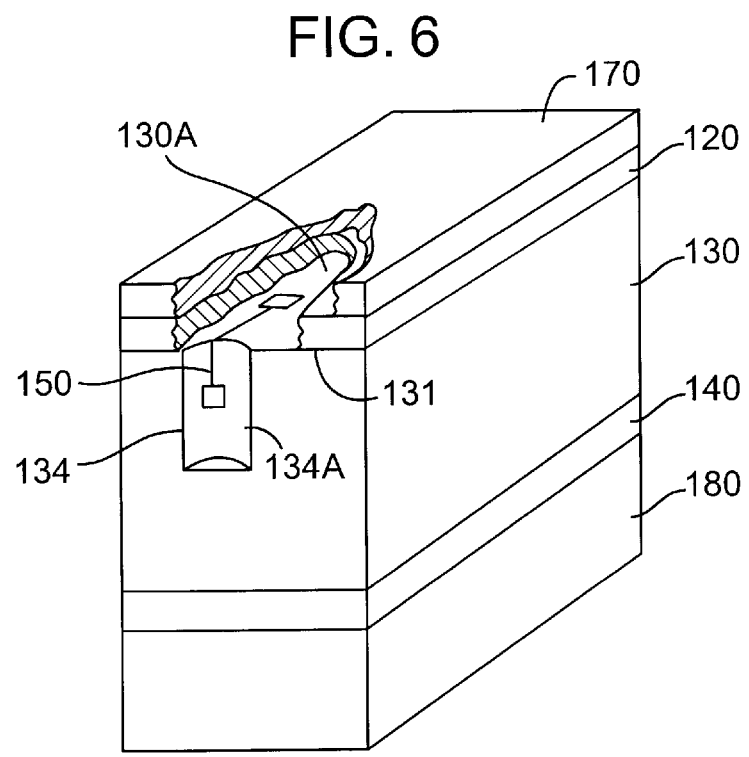

PZT OFF-APERTURE BONDING TECHNIQUE

BACKGROUND OF THE INVENTION

1. Field of the Invention

The present invention relates generally to medical devices and methods for their fabrication. In particular, the invention relates to a transducer which has an improved external connection configuration for making an electrical connection to an imaging catheter.

2. Description of the Relevant Art

Intravascular imaging catheters, generally include one or more ultrasonic transducers which are capable of generating a high-frequency electrical signal, on the order of 30 MHZ, which is used to generate an image. The transducers may be front looking i.e. axially mounted so that an ultrasound beam is transmitted principally along the catheter axis, or side-looking i.e. mounted so that an ultrasound beam is transmitted in a direction perpendicular to the catheter axis.

In one example, a rotatable, side-looking ultrasonic transducer assembly 10, as shown in FIGS. 1A–1C, includes a single transducer element 12. The function of transducer element 12 is to produce and receive an ultrasound pulse. An ultrasound beam is projected radially outward, normal to the surface of transducer element 12. Transducer element 12 is then rotated about an axis of the vessel to scan the interior of the blood vessel wall. Transducer element 12 detects reflections within the ultrasound beam from the vessel wall which are converted to a cross-sectional image of the vessel.

Transducer element 12 is typically configured as a thin, rectangular sheet, which is fabricated from a piezoelectric material. Front and back surfaces of transducer element 12 are covered with thin film electrodes 14 and 16, respectively. As is well known, when a voltage is applied to electrodes 14 and 16, transducer element 12 vibrates to generate pulses at a resonant frequency determined by the mechanical and piezoelectric properties of transducer assembly 10. Conversely, when transducer assembly 10 receives an ultrasonic pulse, an imaging signal, in the form of a voltage pulse, is generated on electrodes 14 and 16 which may be amplified and transmitted to a video or other image generating system.

The external connection of leads to transducer assembly 10 to a lead 60, as shown in FIG. 1C, is of particular interest to the present invention. Lead 60 is coupled to the upper electrode 14 using a manually applied, conductive adhesive 18, usually an epoxy bond formulation including silver. The conductive epoxy 18 provides both a bond and an electrical path from the lead to upper electrode 14. In most cases, a matching layer 15, is formed over the upper electrode 14 prior to connecting external lead 60. In such cases, matching layer 15 must be formed from an electrically conducting material in order to provide the necessary conductive path between lead 60 and upper electrode 14.

Transducer element 12 is mounted within a receptacle 68 formed in a rotatable housing 24 using a bed of conductive adhesive filler 26. A second lead 62 is coupled to housing 24 which is electrically grounded to electrode 16 through the conductive adhesive filler 26. In this way, electrical connections to both electrodes 14 and 16 can be brought out through leads 60 and 62, respectively.

To form high-quality intravascular images, the active surface of the upper electrode 14, with or without matching layer 15 in place, should be kept relatively free of obstructions. The above-described external connection configuration has been successfully implemented in transducer assemblies that are used in relatively large diameter catheters having diameters ranging from about 3 F to about 10 F. The presence of epoxy bond material 18 over the active surface of transducer element 12 has not typically interfered with image quality since the surface area occupied by bond material 18 is small relative to the remaining surface area of active transducer element 12 available for transmission and reception. Accordingly, preciseness and consistency in sizing and locating of the epoxy bond on the transducer element surface during assembly has been of minor importance.

To access small coronary and other arteries, however, "low profile" catheters must be used. These catheters have small diameters, ranging from about 3 F to about 1 F. Small diameter catheters, in turn, require the use of smaller transducer assemblies which have correspondingly smaller active surface areas which can range from about 0.030 in. in width to about 0.010 in. in width. As the transducer element size is reduced, the relative space available on the active surface for external connection is substantially diminished. As the bond material occupies a proportionately larger amount of the available active surface area, the image and its usefulness are degraded. This, in turn, increases the importance of making smaller, uniformly sized, and precisely located bonds.

Unfortunately, reducing the bonding area used for external connection reduces the bond strength between the lead and the transducer and renders bond characteristics, such as electrical resistance, more variable. While improving the quality of the bond would help the problem, the ability of technicians to make smaller, consistently sized and precisely located bonds, without sacrificing the strength and quality of the connection is limited.

Current methods for external lead connection have still other disadvantages when used with very small transducers. For example, inconsistent silver epoxy bond and matching layer ingredient formulations cause variation in transducer performance. Moreover, inconsistent size and placement of the bond causes significant part-to-part variation in performance and is not suitable for producing imaging catheters with repeatable characteristics.

For these reasons it would be desirable to provide improved transducer assemblies, methods for manufacturing such assemblies, and catheter systems incorporating the assemblies, where the transducer has an improved external connection configuration which provides an external connection removed from the active surface of the transducer assembly. It would also be desirable to provide such assemblies and methods which remove the need for using a conductive matching layer and/or a conductive backing layer. Finally, it would also be desirable to provide methods and assemblies which provide consistent part-to-part transducer element performance with repeatable imaging characteristics.

SUMMARY OF THE INVENTION

The present invention provides a transducer assembly having an improved external connection configuration, a method for manufacturing such a transducer assembly, and a catheter system incorporating the transducer assembly. Generally, the improved connection configuration is achieved by creating a conductive path from an upper electrode of the transducer to an electrically conductive notch surface formed on an edge of the transducer assembly so that an external electrical lead can be attached to the active portion of the transducer element via the path. The present invention thus significantly reduces many problems associated with the current method for externally connecting leads to the transducer element, especially the problems encountered when the method is used with very small transducers. For example, the improved external connection removes the need for applying an electrical lead directly to the active surface. Thus, the bond material obstruction of the active transducer element surface, caused by excessive amounts of bond material, which occupy a proportionately large amount of the available active surface area on small transducers is eliminated.

The improved connection configuration also removes the need for using an electrically conductive matching layer or backing element. The matching layer, which typically supplies the conductive path from the lead to the upper active surface, need no longer be conductive, since the improved connection configuration supplies the direct electrical path to the upper active surface in place of the matching layer. Eliminating the requirement for an electrically conductive matching layer in the signal path reduces variations in transducer performance. This, in turn, makes the transducer more suitable for producing imaging catheters with repeatable performance characteristics. Using a non-conductive matching layer also broadens the choice of matching layer materials and the manufacturing process steps. Moreover, the improved connection provides consistently located bonds which creates consistent part-to-part transducer element performance and allows for producing imaging catheters with repeatable characteristics.

In one aspect of the invention, a method is provided for fabricating a transducer assembly having an improved external connection configuration. The transducer assembly is suitable for use with an intravascular catheter. The method includes providing a layer of piezoelectric material which has a first active surface, a second active surface, and a side wall. A notch is formed on a portion of the side wall. The notch defines a notch surface, which intercepts a peripheral edge portion of the first active surface. The method also includes forming conductive layers over the first active surface, the second active surface, and the notch surface. Preferably, the conductive layer formed over the first active surface is in electrical contact with the conductive layer formed over the notch surface. Advantageously, the conductive layer formed over the first active surface and the conductive layer formed over the notch surface are formed as a single, unitary conductive layer.

In an exemplary embodiment of the invention, a transducer assembly, for use with an intravascular catheter, is provided which has an improved external connection configuration. The assembly includes a piezoelectric transducer element having oppositely facing first and second active surfaces and a side wall. A notch is formed on a portion of the side wall, where the notch defines a notch surface that intercepts a plane defined by the first active surface. The assembly also includes a first electrode, formed over the first active surface; a second electrode, formed over the second active surface; and a third electrode, formed over the notch surface. The first electrode formed over the first active surface is in electrical contact with the third electrode formed over the notch surface.

In an alternative embodiment, a second notch is formed on a portion of the side wall of the transducer element. The second notch defines a second notch surface which intercepts a plane defined by the second active surface. A fourth electrode is formed over the second notch surface, which is in electrical contact with the second electrode.

In yet another embodiment of the invention, an improved ultrasonic catheter system is provided, of the type including a transducer assembly having an active transducer element with a first electrode and a second electrode on active surfaces thereof. The improvement includes a notch formed on an edge surface of the active transducer element, where the notch defines a notch surface and a third electrode, formed over the notch surface, which is in electrical contact with the first electrode.

BRIEF DESCRIPTION OF THE DRAWINGS

FIG. 1C is a cross-sectional view of the electrical connection to a standard transducer where the transducer has a matching layer;

FIGS. 2 and 2A illustrate a perspective view of the improved transducer assembly which has an improved external connection configuration according to the present invention;

FIG. 5 illustrates a perspective view of an alternative embodiment of the improved transducer assembly which has a dual improved external connection configuration according to the present invention; and FIG. 6 illustrates a perspective view of an alternative embodiment of the improved transducer assembly which has an improved external connection configuration according to the present invention.

DESCRIPTION OF THE SPECIFIC EMBODIMENT

Figure 1A:
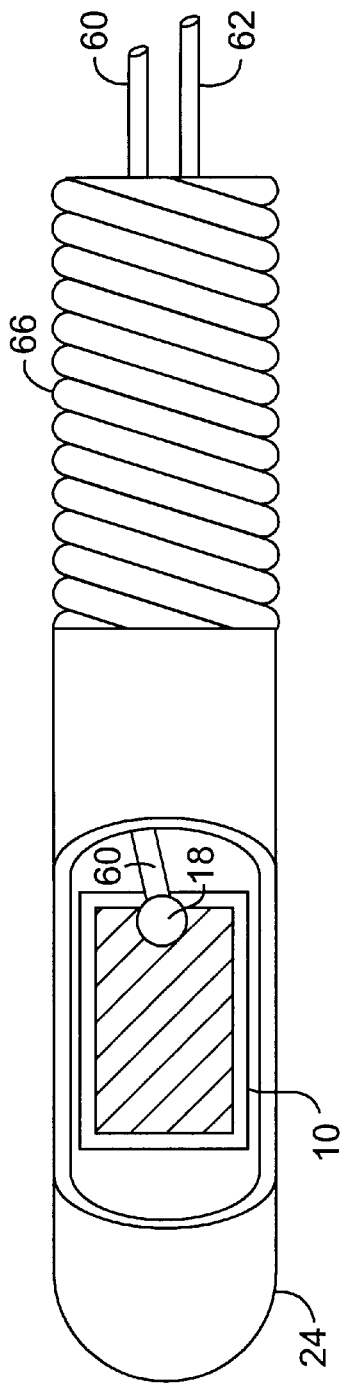
FIGS. 1A and 1B are top and cross-sectional views, respectively, of the electrical connection to a standard transducer mounted in a housing.

Referring now to FIGS. 2 and 2A, a transducer assembly 100 is shown with an improved external connection configuration according to the present invention. The improved external connection configuration provides an attachment surface for lead 165, removed from the top layer of transducer assembly 100, and placed on a side portion of the transducer assembly.

Transducer assembly 100 is typically formed as a layered structure having a lead zirconate titanate (PZT) transducer element 130 sandwiched between other layers that electrically and acoustically interact with the transducer element. Electrodes 120 and 140 are formed over upper and lower active surfaces 130A and 130B of transducer element 130, typically as film layers, which are described in more detail below. Transducer assembly 100 has a cut-out portion which forms a notch 134 on a surface 132A of a side wall 132 of transducer element 130. The internal wall portion of notch 134 defines a notch surface 134A. An electrode 136 is formed over notch surface 134A. As illustrated in FIG. 2A, electrode 136 is configured such that it is in direct electrical contact with the upper active surface electrode 120. Accordingly, notch electrode 136 provides a direct electrical path from electrical lead 165 through notch electrode 136 to the first electrode 120. Lead 165 can be bonded to notch electrode 136 using conventional bonding materials such as silver epoxy bond and the like. In a preferred embodiment, electrodes 120 and 136 are formed as one continuous electrode.

Figure 1B:
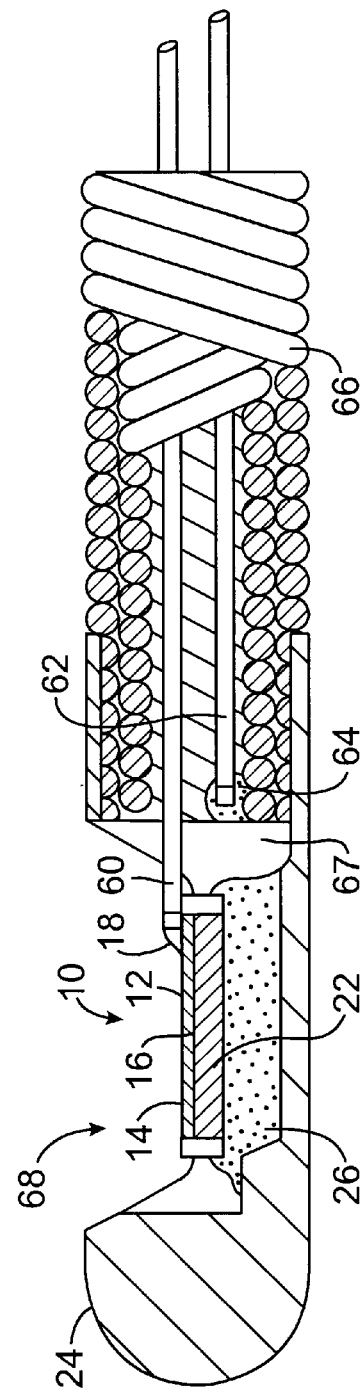

In most cases, transducer assembly 100 has a matching layer 170 formed over an upper surface of the first electrode 120 and/or a backing element 180 attached to second electrode 140. Backing element 180 both attenuates ultrasonic energy from the back face of transducer assembly 100 and facilitates mounting of transducer assembly 100 in the distal housing of a catheter. For example, transducer assembly 100 may be mounted within the receptacle 68 of a catheter, generally as shown in FIG. 1B.

Figure 3A:
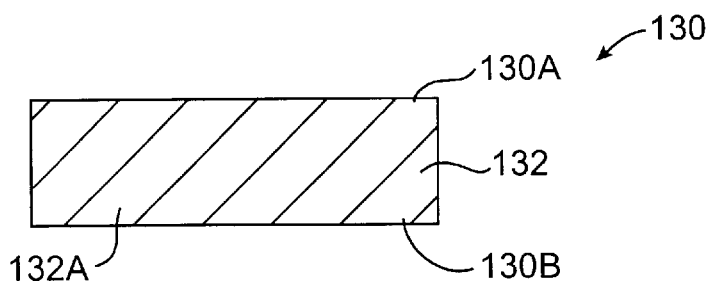
FIGS. 3A–3D show cross-sectional views of a portion of a transducer undergoing subsequent steps in the fabrication of the transducer assembly as in FIG. 2, with an improved external connection configuration according to the present invention.
Figure 3B:
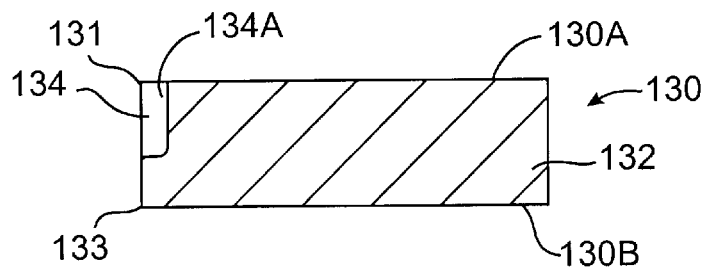

FIGS. 3A–3D, illustrate a method for manufacturing transducer assembly 100 having the improved external connection configuration of the present invention. Conveniently, multiple transducer elements can be fabricated simultaneously from a large sheet of PZT material. A PZT layer will typically be configured as a rectangular sheet which is 0.75 in. by 0.75 in. in size and can be ground or machined down to any desired thickness, preferably about 0.002 in. to about 0.009 in. Individual PZT transducer elements 130 are separated from the PZT material, typically by cutting or dicing and can be cut into a variety of shapes, such as circular, square, rectangular, elliptical, oval, or any other suitable geometry. As is shown in FIG. 3A, PZT transducer element 130 has a first active surface 130A and a second active surface 130B. Surfaces 130A and 130B face in opposite directions. The PZT transducer element also has side walls 132 which provide a side wall surface 132A, typically normal to surfaces 130A and 130B. The PZT transducer element 130 may be formed from any suitable piezoelectric material, preferably being made from conventional materials, such as PZT or other piezoceramic materials, quartz or other single crystal materials, piezocomposites, or piezoelectric polymers.

After PZT transducer element 130 has been suitably formed, a portion of side wall 132 is removed from a side wall 132A of PZT transducer element 130 to form notch 134. The internal wall of notch 134 defines notch surface area 134A. Notch surface area 134A is formed into any suitable geometry. In a preferred embodiment, notch surface 134A will provide a smooth, flat surface suitable for forming an electrode thereon. As can be best understood from FIG. 3B, notch 134 extends from a peripheral edge 131 of first active layer 130A to an appropriate point on side wall surface 132A. Notch surface 134A is large enough to accommodate the attachment of lead 165. Although the length of the notch will vary depending on the size of transducer element 130 and other factors, it is preferably approximately 10% of the side wall length or 0.003 to 0.005 inches. In an alternative embodiment, notch 134 extends the entire length of side wall 132 to a peripheral edge 133 of surface 130B. This embodiment is described in more detail below. Well known semiconductor machining techniques are used to form notch 134, such as laser cutting, dicing, or similar methods, using commercially available equipment. The depth of the notch can vary between 0.015 and 0.006 inches, depending on such factors as, for example, the size of transducer element 130 or the size of lead 165. Preferably the depth will be about 0.002" or about 60–70% of the transducer element thickness.

Figure 3C:
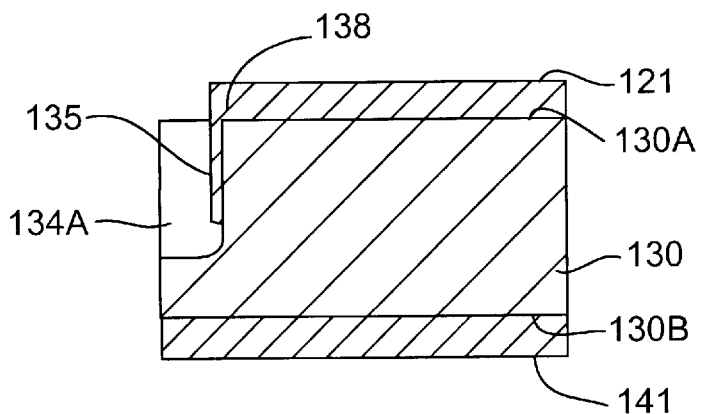

Typically after forming notch 134, conductive films 121 and 141 are formed over upper active surface 130A and lower active surface 130B, respectively as shown in FIG. 3C. A conductive film 135 is also formed over notch surface 134A. Conductive film layers 121 and 135 can be formed separately or, preferably, layers 121 and 135 are formed simultaneously to create one single, unitary film layer 138. The unitary film layer 138 forms the first electrode 120 and lower film 141 forms second electrode 140. The conductive layers may be applied by well known fabrication techniques, such as flashing, electroplating, vacuum deposition, metallic thin-film deposition, evaporation, sputtering and the like. The films can be made of any conductive material, but preferably are made of gold and chrome, or gold and chrome and nickel (preferably gold on chrome, or gold on chrome and nickel; chrome, or chrome and nickel, for adhesion, and gold for conductivity). The effective depth of the film layers 121, 141, and 135 can be very small, typically having a maximum depth of between about 2000 and about 8000 Å, preferably about 3000 Å. Preferably, the film layer will include about 200 Å of chrome, and about 3000 Å of gold.

Lead 165 is bonded to electrode 120 in the notch area. As mentioned above, lead 165 can be bond using many conventional bonding techniques.

Figure 3D:
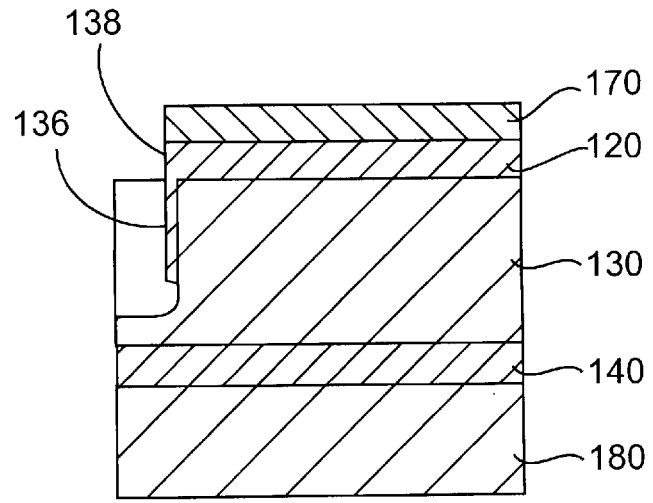

In most cases, a matching layer 170 is formed over first electrode 120, as is shown in FIG. 3D. However, the matching layer may not cover the portion of electrode 120 extending into notch 134. Preferably, after optionally applying non-conductive matching layer 170 to the top portion of first electrode 120, the matching layer 170 may be ground down or otherwise machined, if needed, such that its thickness is made equal to any predetermined fraction of the ultrasonic wavelength emitted by the transducer. Preferably, the thickness can be made equal to, but is not limited to, about one-quarter of the predetermined ultrasonic signal wavelength. Thus, in an exemplary embodiment, the thickness of the matching layer 170 can typically have a maximum thickness of between 10 and 100 $\mu$m, depending on the frequency of operation, and speed of sound in the matching layer material. In some cases, multiple matching layers 170 may be applied to the first active surface of the piezoelectric layer and used in conjunction with one another. Each additional matching layer may also have a thickness made equal to any predetermined fraction of the ultrasonic wavelength emitted by the transducer.

Figure 4:
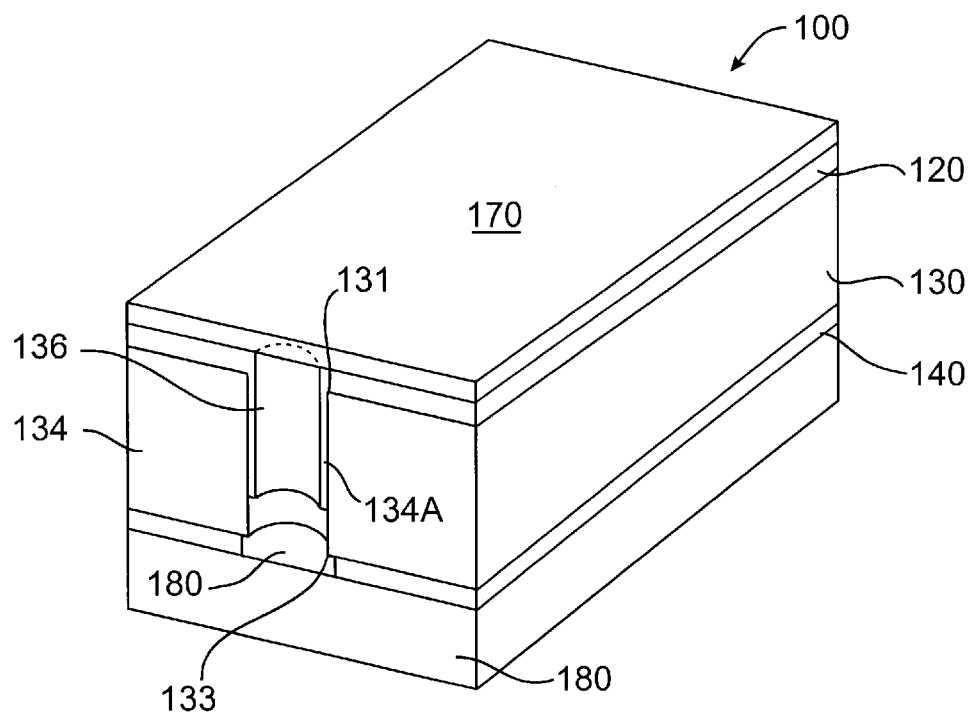
FIGS. 4 and 4A illustrate a perspective view of an alternative embodiment of the improved transducer assembly which has an improved external connection configuration according to the present invention.
Figure 4A:
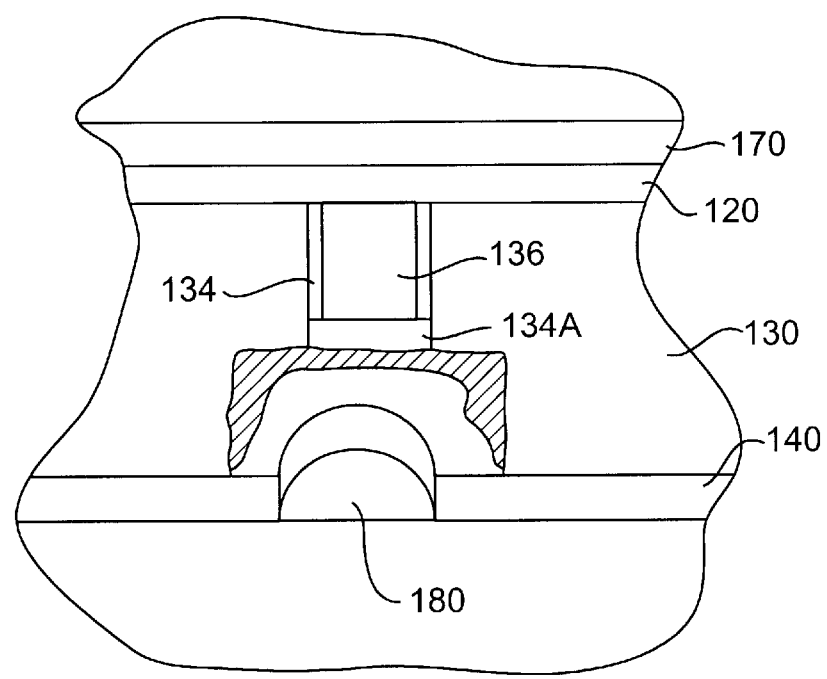

In an alternate embodiment of improved transducer assembly 100, notch 134 extends from an edge portion 131 of first active surface 130A to an edge portion 133 of second active surface 130B. As shown in FIG. 4, electrode 136 is formed over a portion of notch surface 134A. As shown in FIG. 4A, a short circuit between notch electrode 136 and second electrode 140 is avoided since a portion of second electrode 140 proximate to edge portion 133 is removed. The fabrication process of notch 134 is simplified since notch 134 to extend the entire length of the PZT transducer element.

In another alternative embodiment, two external connections are configured on side wall 132 of PZT transducer element 130. As shown in FIG. 5, PZT transducer element 130 has two notches 134 and 145 formed on side wall 132. First and second notches 135 and 145 are formed in the manner described above. Second notch 145 has conductive film layer 137 formed over second notch surface 145A. Conductive layer 137 provides an electrical pathway to conductive layer 141. Preferably, the conductive layers 137 and 141 are combined into single, unitary second electrode 140. Thus, the need for using a conductive backing element 180 is removed. Although notches 134 and 145 are shown formed adjacent to each other in the exemplary embodiment, each notch could be formed on any suitable side wall surface 132A of PZT transducer element 130.

The invention has now been described with reference to a specific embodiment. However, the invention is not intended to be so limited. Although the invention was described as being extremely useful with small transducers sized, the improved external connection can work with any sized transducer assembly.

Alternatives and substitutions will also be apparent to persons of skill in the art. For example, as shown in FIG. 6, electrode 150 can be formed as a wire or other conductive material instead of the conductive layer. In this case, wire 150 is applied to notch surface 134A and bent over edge 131 or otherwise formed to lie on top of first active surface 130A. Conductive layer 121 is formed over active surface 130A and is made to contact wire 150. Wire 150 provides the electrical path to conductive layer 121. Accordingly, the invention is not intended to be limited except as provided by the appended claims.

What is claimed is:

1. A method for fabricating a transducer assembly said method comprising:

providing a layer of piezoelectric material having a first active surface, a second active surface, and a side wall;

forming a notch on a portion of the side wall, the notch defining a notch surface which intercepts a peripheral edge portion of the first active surface; and forming conductive layers over the first active surface, the second active surface, and the notch surface, wherein the conductive layer formed over the notch surface is in electrical contact with the conductive layer formed over the first active surface but not with the conductive layer formed over the second active surface.

2. The method as in claim 1, further comprising applying at least one matching layer to the first active surface of the piezoelectric layer.

3. The method as in claim 2, wherein applying comprises applying at least one matching layer is formed to have a thickness equal to a fraction of a predetermined ultrasonic signal wavelength emitted from the first active surface.

4. The method as in claim 1, further comprising applying a plurality of matching layers to the first active surface of the piezoelectric layer, each of said plurality of matching layers having a thickness equal to a fraction of a predetermined ultrasonic signal wavelength emitted from the first active surface.

5. The method as in claim 2, wherein applying comprises applying at least one matching layer is made of a non-conductive material.

6. The method as in claim 1, further comprising bonding the second active surface of the piezoelectric layer to a backing element.

7. The method as in claim 1, further comprising bonding a lead to the conductive layer formed over the notch surface.

8. The method as in claim 1, wherein forming the conductive layer comprises forming a conductive material taken from the group comprising of gold, chrome, and nickel.

9. The method as in claim 1, wherein providing the piezoelectric layer comprises providing a material taken from the group comprising of PZT and other piezoceramic materials, quartz and other single crystal materials, piezo-composite materials, and piezoelectric polymers.

10. The method as in claim 1, further comprising:

forming a second notch on a portion of the side wall, the second notch defining a second notch surface which intercepts an edge portion of the second active surface; and forming a conductive layer over the second notch surface, wherein the conductive layer formed over the second notch surface is in electrical contact with the conductive layer formed over the second active surface but not with the conductive layer formed over the first active surface.

11. The method as in claim 1, wherein the notch surface extends substantially the length of the side wall and intercepts a peripheral edge portion of the second active surface.

12. A transducer assembly, for use with an intravascular catheter, having an improved external connection configuration, the transducer assembly comprising:

a piezoelectric transducer element having oppositely facing first and second active surfaces and a side wall;

a notch formed on a portion of the side wall, the notch defining a notch surface which intercepts a plane defined by the first active surface;

a first electrode formed over the first active surface;

a second electrode formed over the second active surface; and a third electrode formed over the notch surface, wherein the first electrode formed over the first active surface is in electrical contact with the third electrode formed over the notch surface.

13. The transducer assembly of claim 12, further comprising:

a second notch formed on a portion of the side wall, the second notch defining a second notch surface which intercepts a plane defined by the second active surface; and a fourth electrode formed over the second notch surface, wherein the second electrode is in electrical contact with the fourth electrode.

14. The transducer assembly of claim 12, wherein the notch surface intercepts a peripheral edge portion of the second active surface.

15. The transducer assembly of claim 12, wherein the first electrode formed over the first active surface and the third electrode formed over the notch surface form one single, unitary electrode.

16. The transducer assembly as in claim 12, further comprising at least one matching layer to the first active surface of the piezoelectric layer.

17. The transducer assembly as in claim 16, wherein the at least one matching layer is formed to have a thickness equal to a fraction of a predetermined ultrasonic signal wavelength emitted from the first active surface.

18. The transducer assembly as in claim 16, wherein the at least one matching layer comprises a plurality of matching layers, each of said plurality of matching layers having a thickness equal to a fraction of a predetermined ultrasonic signal wavelength emitted from the first active surface.

19. The transducer assembly of claim 12, further comprising a backing material bonded to the second active surface of the transducer element.

20. The transducer assembly of claim 12, wherein the electrodes are made of a material taken from the group of a conductive material comprising of gold, chrome and nickel.

21. The transducer assembly of claim 12, wherein the piezoelectric transducer element comprises a material taken from the group comprising PZT and other piezoceramic materials, quartz and other single crystal materials, piezo-composite materials, and piezoelectric polymers.

22. A transducer assembly, for use with an intravascular catheter, having an improved external connection configuration, the transducer assembly comprising:

a piezoelectric transducer element having oppositely facing first and second active surfaces and a side wall;

a notch formed on a portion of the side wall, the notch defining a notch surface;

a conductive element formed on a portion of the notch surface and the first active surface; and conductive layers formed over the first active surface and the second active surface; wherein the conductive layer formed over the first active surface is in electrical contact with the conductive element.

23. An improved ultrasonic catheter system of the type including a shaft carrying a transducer assembly comprising an active transducer element having a first electrode and a second electrode on active surfaces thereof and at least one lead connected to the transducer element, the improvement comprising:

a notch formed on an edge surface of the active transducer element, the notch defining a notch surface; and a third electrode formed over the notch surface, wherein the third electrode formed over the notch surface is in electrical contact with the first electrode and the at least one lead is connected to the third electrode.

* * * * *